United States Patent
Hall et al.

(10) Patent No.: US 8,424,394 B2
(45) Date of Patent: Apr. 23, 2013

(54) AIR SAMPLING TUBE

(75) Inventors: David L. Hall, Luther, MI (US); Peter Stouffer, Holly, MI (US); James E. Ludwig, Hasilngden Lancashire Bb4 4pw (GB)

(73) Assignee: Apollo America, Auburn Hills, MI (US)

( * ) Notice: Subject to any disclaimer, the term of this patent is extended or adjusted under 35 U.S.C. 154(b) by 490 days.

(21) Appl. No.: 12/540,550

(22) Filed: Aug. 13, 2009

(65) Prior Publication Data
US 2011/0036445 A1 Feb. 17, 2011

(51) Int. Cl.
*G01N 1/00* (2006.01)
(52) U.S. Cl.
USPC .......................................................... 73/863
(58) Field of Classification Search ........................ None
See application file for complete search history.

(56) References Cited

U.S. PATENT DOCUMENTS

| | | | | | |
|---|---|---|---|---|---|
| 3,579,794 | A | * | 5/1971 | Powell | 29/237 |
| 3,782,200 | A | * | 1/1974 | Maas | 73/863.51 |
| 5,703,301 | A | * | 12/1997 | Pinto et al. | 73/864.63 |

* cited by examiner

*Primary Examiner* — Peter Macchiarolo
*Assistant Examiner* — Alex Devito
(74) *Attorney, Agent, or Firm* — Gifford, Krass, Sprinkle, Anderson & Citkowski, P.C.

(57) ABSTRACT

An air sampling tube is provided that provides superior air flow, strength, and manufacturability and couples to an air sampling sensor housing. The sidewall of the tubular section has an axially extending groove. To facilitate installation and inspection, an air sampling tube is provided with a starter cap. An end cap prevents air flow through the distal end of the tube. An air sampling tube is provided that assures proper axial positioning of tubular section apertures through resort to a coupler with a rotationally asymmetric joining element. A modular kit is provided that allows for custom installation without resort to cutting or forming operations in the field.

13 Claims, 10 Drawing Sheets

AIR SAMPLING TUBE

FIELD OF THE INVENTION

The present invention relates in general to a tube for conveying air between a forced air supply and a housing containing a detector and in particular to a tube assuring correct alignment and providing high efficiency of air flow.

BACKGROUND OF THE INVENTION

The sampling of air within the air handling system of a structure is essential to the early detection of air quality dangers such as smoke or carbon monoxide. A conventional scheme for air sampling includes a housing containing a duct air quality detector such as a smoke detector, carbon monoxide detector or other types of air quality detectors such as particulate, humidity, or oxygen. A conventional duct detector housing is exposed to air from an air handling system by way of a sampling tube extending into a duct of the air handling system. The duct detector housing includes an exhaust port so as to create air flow through the detector housing. The housing exhaust port is often coupled to the duct being sampled so as to create a return flow of the sampled air back into the air handling system. Conventionally, an air handling tube is custom formed to accommodate duct dimensions relative to the housing. The tube is formed from an extended length of periodically perforated tubing. FIG. 1 depicts a conventional prior art duct detector housing equipped with conventional air sampling tubes and coupled to an air handling system duct.

Conventional air sampling tubes of a needed length are cut from periodically perforated tubing having a length greater than any that is anticipated to be used. This approach is not only wasteful of tubing material, but also requires field work to cut the tubing, and presents logistical problems associated with the transport and handling of tubing having a length of, for example, 5 feet. Alternatively, conventional air sampling tube construction has involved joinder of rotationally a specific sections of pre-apertured tubing as detailed in, for example, prior art FIG. 1. Regardless of construction, periodically perforated tubing is prone to hole fouling associated with particulate in the air handling system and in the instance of galvanized steel tubing the hole formation compromises coating protective integrity. The custom nature of assembly of an air sampling tube poses a problem of assuring proper hole directionality about a tube axis. This rotational symmetry increases both installation and inspection effort.

Thus, there exists a need for an air sampling tube having a tubular section that is only joined to another component in a unique orientation relative to an aperture in the tubular section. There further exists a need for an air sampling tube that has a tubular extension with an axially extending groove defined by edges where at least one of the edges is enveloped to form an eddy channel adjacent to the groove. Still further, there exists a need for an assembler or inspector to be able to identify the axial position of air intake holes on a tubular section without resort to movement of the air sampling tube.

SUMMARY OF THE INVENTION

An air sampling tube is provided that provides superior air flow, strength, and manufacturability and couples to an air sampling sensor housing. The tube in simplest form is a tubular section having a sidewall defining a tube interior and tube exterior. The sidewall of the tubular section has an axially extending groove defined by a first edge and a second edge. At least one of the edges is enveloped within the tube interior to form an eddy channel adjacent to the groove. The tubular section is adapted to join to the housing.

To facilitate installation and inspection, an air sampling tube is provided that includes a tubular section having a sidewall defining a tube interior and a tube exterior with at least one aperture through the sidewall providing air communication therebetween. A starter piece is provided having a choke partially occluding air flow within the starter piece and having a shaped aperture indicative of the orientation of the at least one aperture. The starter piece is joined intermediate between the tubular section and an air sampling sensor housing. The distal end of the tubular section relative to the housing engages a coupler for receipt of another tubular section or an end cap occluding air flow through the distal end.

An air sampling tube is provided that assures proper axial positioning of tubular section apertures and includes a first tubular section having a sidewall defining a tube interior and a tube exterior and at least one aperture providing air communication therebetween. At least one rotationally asymmetric joining element is associated with an end of the first tubular section or a coupler secured to the tubular section end. A component is also provided having a component end with complementary tab or complementary groove to the at least one rotationally asymmetric joining element to only form a complete engagement directly with the first tubular section or the intermediate coupler in a single rotational orientation.

DETAILED DESCRIPTION OF THE PREFERRED EMBODIMENTS

The present invention has utility as an air sampling tube to draw a continuous aliquot of air from an air handling system to convey the aliquot to a housing containing an air sampling sensor. The present invention can address a number of limitations found in conventional air sampling tubes, and the inventive improvements include assurance of directionality of an air instance aperture within a tubular section of an air sampling tube; superior mechanical strength and air flow characteristics of a tubular section; modular assembly; and a choke allowing for the visual confirmation of aperture directionality without resort to movement of a tubular section of the air sampling tube. Each of these attributes of an inventive tube is operative independent of the others. An additional attribute of an inventive air sampling tube is the ability to provide an assembler with a component kit allowing for customization of the air sampling tube without resort to tools to cut or otherwise modify inventive tube elements to satisfy the geometries of a given air handling system and the relative position of an air sampling sensor housing.

Figure 1:
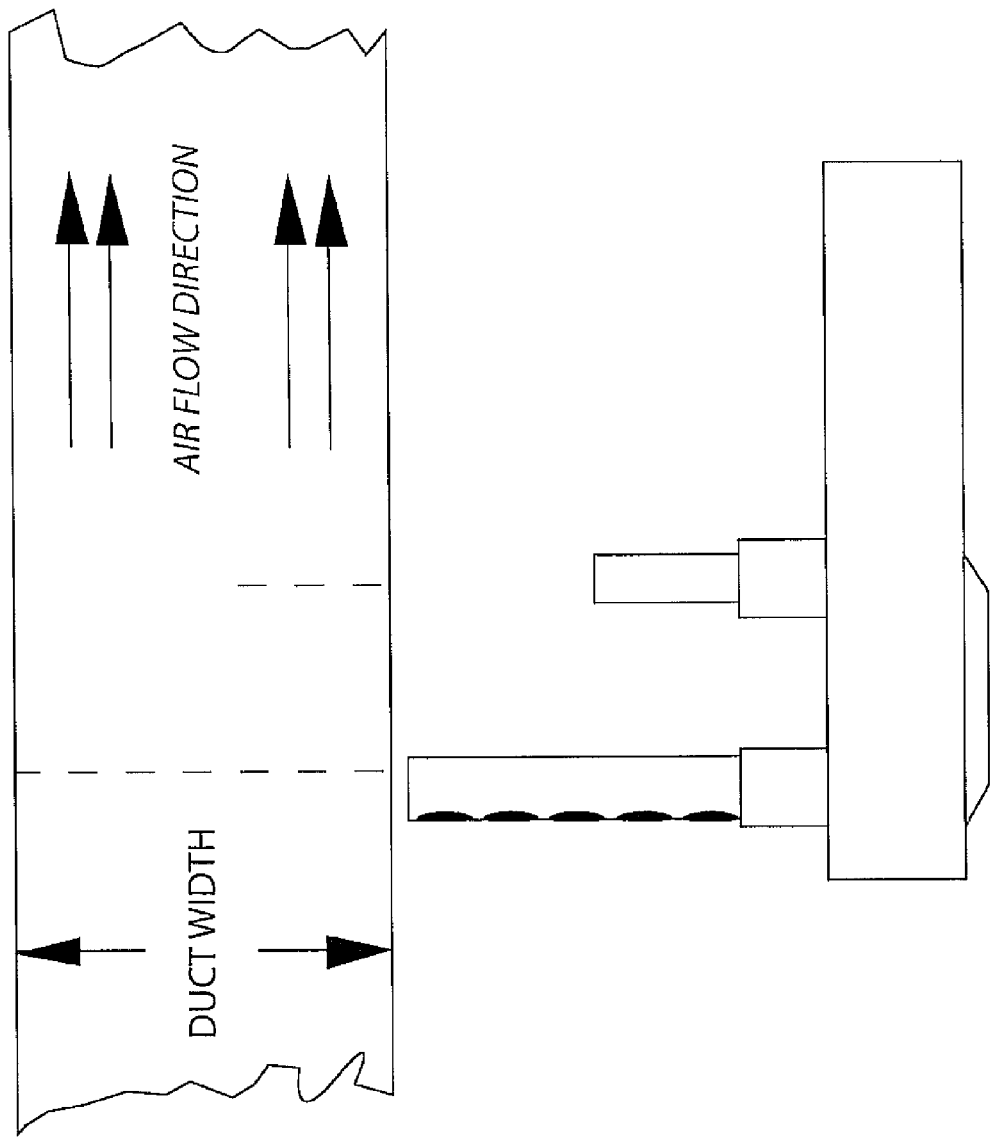
FIG. 1 is a perspective view of a prior art duct detector housing in fluid communication with a conventional air sampling tube.
Figure 2A:
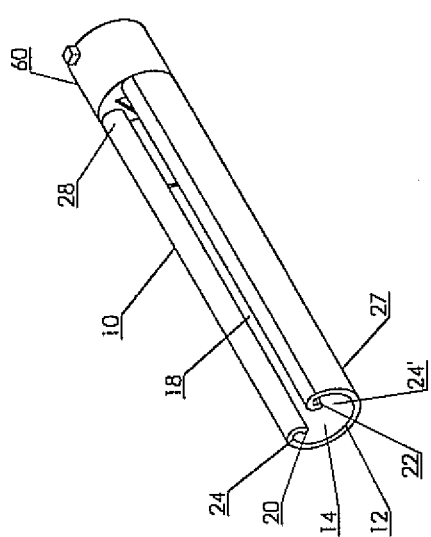
FIG. 2A is a perspective view of an inventive tube of a tubular section with a symmetric cross section and two eddy channels and mated to a starter section for engaging a duct detector housing.
Figure 2B:
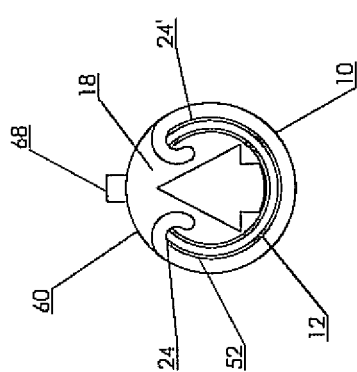
FIG. 2B is an end view of FIG. 2A.

Referring now to FIGS. 2A and 2B, the tubular section of an inventive air sampling tube is shown generally at 10. The tubular section 10 has a sidewall 12 defining a tube interior 14 and an exterior. A groove 18 provides fluid communication along the sidewall 12 between the exterior and the interior 14 and is not subject to the uneven air uptake within a duct or the debris fouling associated with a conventional tube having a uniformly spaced line of round holes. The groove 18 is bounded by a first edge 20 and a second edge 22. It is appreciated that the groove 18 need not extend along the entire length of tubular section 10. Typical widths for a groove 18 are between 0.1 and 2 centimeters. However, it is preferred that the groove extends over the majority of the length of tubular section 10 in uninterrupted form. It has surprisingly been discovered that, unlike conventional periodic apertures, a groove 18 is less prone to fouling than erratically spaced apertures; the fouling associated with dust and other particulate found in an air handling system. In a tubular section 10, preferably at least one of the first edge 20 or the second edge 22 is enveloped within the tube interior 14 to form an eddy channel 24 adjacent to the groove 18. As shown in FIGS. 2A and 2B, eddy channels 24 and 24' are shown being formed in both edges 20 and 22 while an inventive tube is appreciated to be formed with only one such eddy channel. An eddy channel 24 has been formed to more efficiently transmit air through a tubular section 10 relative to a periodically apertured tube or a grooved tube lacking an eddy channel. Additionally, formation of an eddy channel 24 greatly improves the strength of the tubular section 10 relative to a comparable walled circular cross section tube having either periodic apertures or a groove along the length thereof. A tubular section 10 is readily formed from a variety of materials illustratively including steel, aluminum, and copper; thermoplastics such as polyethylene, polyvinylchloride, and polystyrene. It is appreciated that a tubular section 10 is well suited for extrusion formation and is more efficiently produced than forming a tube and then boring periodic apertures therein. Additionally, in instances when a tubular section 10 is formed of steel and anticorrosion coating is applied thereon, the resultant coating is not compromised by subsequent periodic aperture formation. While the tubular section is depicted in the accompanying figures as having a circular cross section, it is appreciated that other shapes such as cross sections that are triangular, rectilinear, and hexagonal are also operative herein. A notched starter cap 60 is coupled to proximal section end 28 to couple the tube 10 to a conventional duct detector housing. The starter 60 is further detailed with respect to FIGS. 5A-5C. Distal end 27 of tube 10 is amenable to engagement to a joinder, an end cap or other modular kit component.

Figure 3:
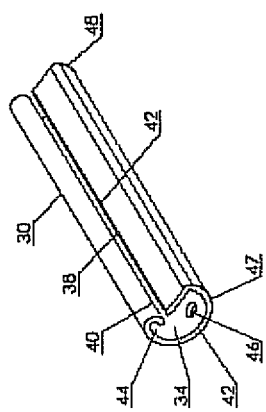
FIG. 3 is a perspective view of an alternate tubular section operative in the present invention with an asymmetric cross section and a single eddy channel.

FIG. 3 shows an alternative inventive tubular section depicted generally at 30. Tubular section 30 is similar to tubular section 10 of FIGS. 2A and 2B that is depicted with a single eddy channel and a second edge extending outward to expand the lateral extent of groove. The tubular section 30 is formed of the same materials as detailed with respect to tube 10. Tubular section 30 has a sidewall 42 defining an interior 34 and an exterior. A groove 38 extends along at least a portion of the length of the tubular section 30 and is bounded by a first edge 40 and a second edge 42. The first edge 40 is enveloped within the tube interior 34 to form an eddy channel 44 adjacent to the groove 38. The second edge 43 is extended outward towards the exterior 36 so as to increase the lateral extent of the groove 38 relative to groove 18 for a given tubular section diameter. Optionally, the second edge 42 is likewise enveloped to form a second eddy channel (not shown). The groove 38 provides air communication between tube exterior and the tube interior 34. Optionally, an aperture 46 is provided proximal to a tubular section end 47 with the aperture 46 adapted to engage a locking tab of another inventive air sampling tube component. A starter cap 60 as detailed with respect to FIG. 2 is readily modified to mateably engage the distal end 48 of the tube 30.

Figure 4A:
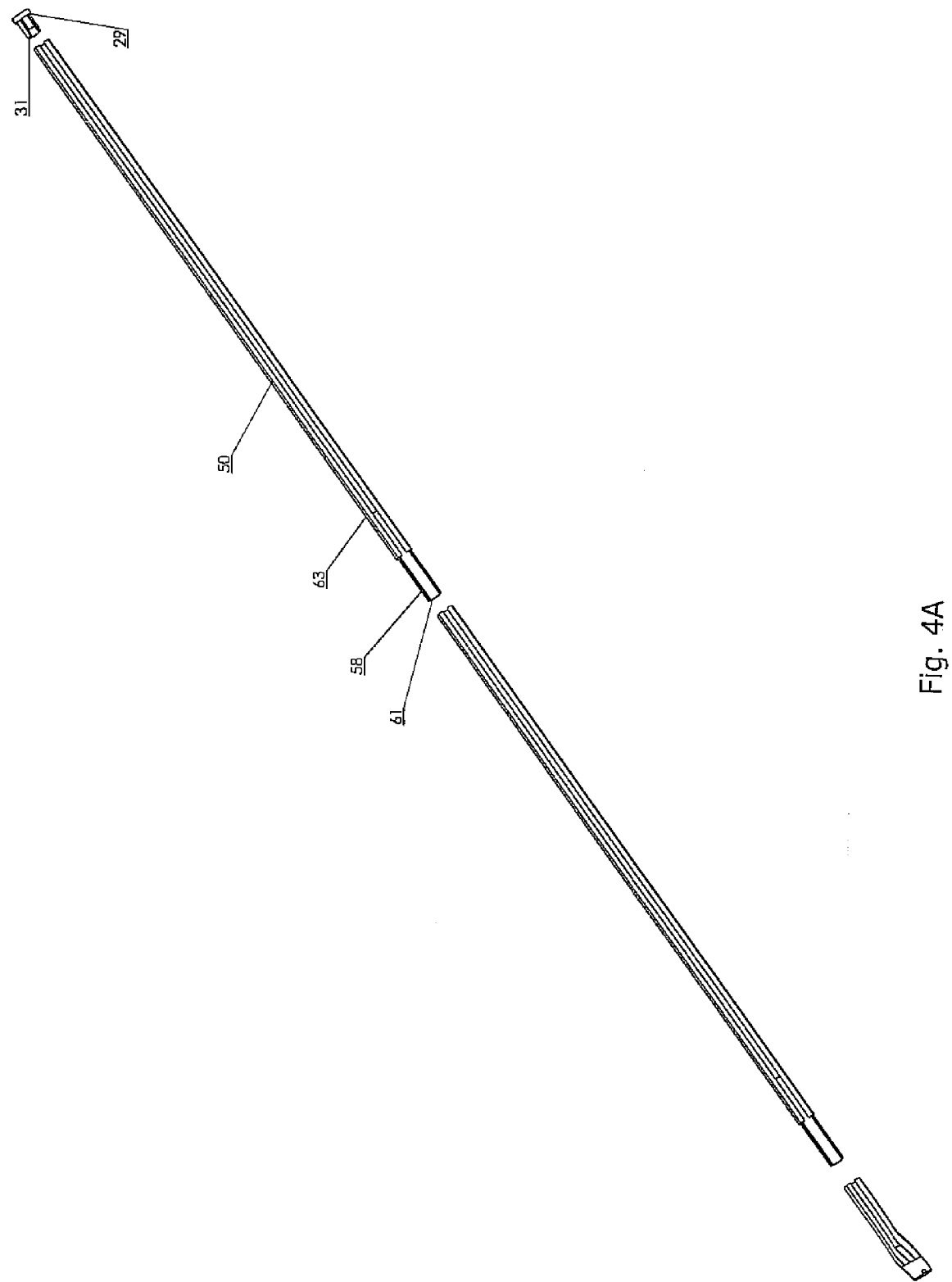
FIG. 4A is an exploded perspective view of an inventive air sampling tube.

A tubular section 10 or 30 is readily coupled to a housing containing an air sampling sensor to form an air sampling tube. An inventive air sampling tube is depicted in FIG. 4A in exploded perspective view generally at 50. Air sampling tube 50 has at least one tubular section such as linear section 10 of FIGS. 2A-2B or tubular section 30 of FIG. 3. For illustrative purposes, FIG. 4A depicts two tubular sections: 10 and a like duplicate section 10' detailed with respect to FIGS. 2A and 2B. However, it is appreciated that one or both of these tubular sections 10 or 10' is readily replaced by a tubular section 30 with an appropriate change in the joinder.

Figure 4B:
FIG. 4B is an end view of a linear coupler shown in FIG. 4A.
Figure 4C:
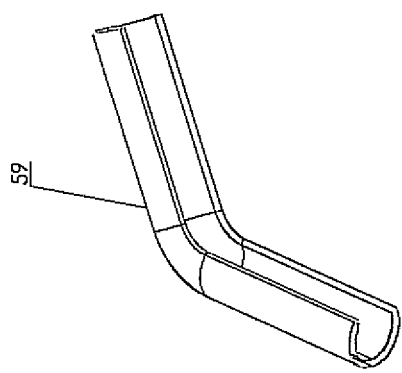
FIG. 4C is a perspective view of an angled coupler for joining a tubular section to other parts of an inventive tube.
Figure 4D:
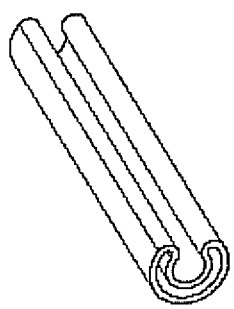
FIG. 4D is a perspective view of a receptacle-like coupler for tubular sections per FIG. 2B.

An end cap 60 is provided to engage an end of tubular section 10. The end cap 60 has a protrusion 52 adapted to engage the wall 12 or 42 of tubular section 10 or 30, respectively. A protrusion 52 preferably inserts within the interior of the tubular section 10 or 30. Optionally, the protrusion 54 has a protrusion edge adapted to engage an eddy channel 24 of the tubular section 10 or eddy channel 44 of the tubular section 30. It is noted that the starter cap 60 is only capable of engaging the tubular section in a single orientation and upon engagement precludes air flow via the distal end of the tubular section and instead only provides fluid communication between the exterior and interior of the tubular section 10 by way of the groove 18 (or 38 of tubular section 30). The air sampling tube 50 is rendered modular by providing a coupler 58 or 59. The coupler 58 or 59 has a tubular section proximal end joinder portion 61 and a tubular section distal end joinder portion 63. The joinder portion 61 forms a semi-cylindrical blade or receptacle complementary to either the proximal end 28 or distal end 27 of tubular section 10; or the proximal end 48 or distal end 47 of tubular section 30. The joinder portion 61 defines a friction fit with the complementary end of the tube section 10 or 30. Adhesive or fusion is optionally used to secure the coupler and tubular section. Joinder portion 63 is formed as a blade or receptacle per portion 61 to join a second tubular portion. A receptacle-type coupler 58' for joining two tubular portions 30 is depicted in perspective view in FIG. 4D. The coupler 58 in end view is depicted in FIG. 4B and matingly engages a wall 12 or wall 42 of a tubular section. Preferably, securement is through friction fitting, although adhesive or fusion is also operative herein. Coupler 59 operates in the same manner as coupler 58 with the exception that the joinder of two tubular sections occurs at a nonlinear angle. The couplers 58 and 59 are both operative in an inventive air sampling tube, each alone or in combination. The couplers 58 and 59 provide a communicative internal bore between joined tubular sections. A tab 68 is provided on starter 60 thereby rendering the resultant air sampling tube 50 suitable for usage with a housing as detailed in U.S. Pat. No. 7,204,522. Alternatively, the starter piece 60 has a recess adapted to engage a complementary engagement element found within the air sampling sensor housing. The air sampling tube 50 as depicted in FIG. 4A is readily provided as a modular kit containing a starter cap 60, an end cap 29, multiple tubular sections 10 or 30, or a combination thereof with the multiple tubular sections being of like or different lengths. With the inclusion in the kit of multiple couplers 58 and 59, and optionally at least one starter piece such as that depicted at 60 or other starter pieces adapted to engage particular makes and models of housings, an installer is able to quickly form a custom air sampling tube without resort to tools. An inventive air sampling tube 50 is optionally terminated with an end cap 29. The end cap 29 has a complementary protrusion 31 engaging a tubular section 10 or 30 to provide a friction fit therewith in a similar manner to portion 52 of starter cap 60. The body 33 of end cap 31 precludes air entry via the distal end into a tubular section 10 or 30 of assembly 50. An end cap 29 is formed of like materials relative to a tubular section 10 or 30, and a starter cap 60.

Figure 5A:
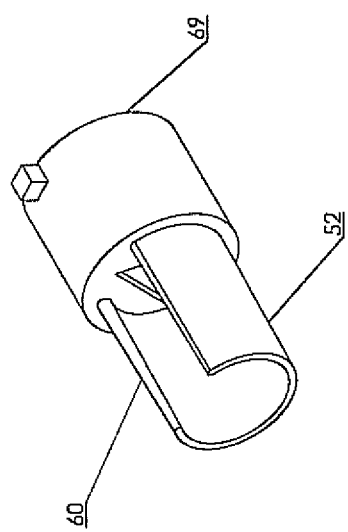
FIG. 5A is a perspective view of a tubular housing starter section.
Figure 5B:
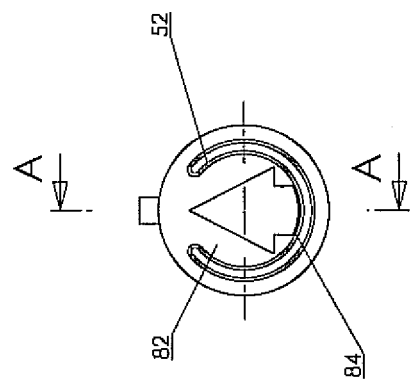
FIG. 5B is an end view into the bore of a tubular housing starter.
Figure 5C:
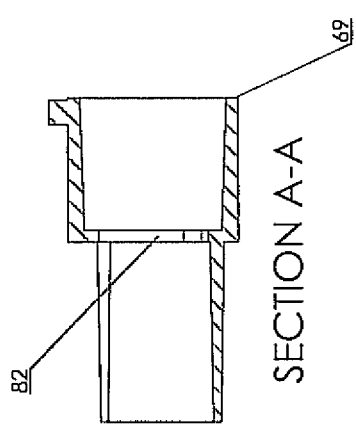
FIG. 5C is a cross-sectional view of the section of FIG. 5B along line A-A.

FIGS. 5A-5C show with detail starter piece 61. A starter piece 61 optionally includes a choke 82 in the bore that partially occludes air flow within the starter piece interior and is visible from front end 69. While it is appreciated that the choke 82 occludes air flow between the air sampling tube 50 and the air sampling sensor housing, a choke 82 having a shape indicative of groove position in a tubular section 10 or 30 greatly facilitates inspection and assurance of correct orientation of the air sampling tube. The choke 82 is optionally painted a different color than the remaining portions of the starter piece 61 to further emphasize directionality. As shown in FIG. 5B, the aperture 84 is arrow shaped within the choke 82 and is intended to point in the direction of the groove 18 with respect to FIG. 4A.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. An air sampling tube comprising:
   a tubular section having a sidewall defining a tube interior and a tube exterior, said sidewall having an axially extending groove defined by a first edge and a second edge of said sidewall, the groove providing air communication between the tube interior and the tube exterior, said tubular section having a proximal tube end and a distal tube end, the proximal tube end joined to a housing having an air sampling sensor, at least one of the first edge or the second edge is enveloped within the tube interior to form an eddy channel adjacent to the groove.

2. The tube of claim 1 wherein both the first edge and the second edge of said sidewall are enveloped within the tube interior forming the eddy channel and a second eddy channel bounding the groove.

3. An air sampling tube comprising:
   a tubular section having a sidewall defining a tube interior and a tube exterior, said sidewall having an axially extending groove defined by a first edge and a second edge of said sidewall, the groove providing air communication between the tube interior and the tube exterior, said tubular section having a proximal tube end and a distal tube end, the proximal tube end joined to a housing having an air sampling sensor and a choke partially occluding air flow in fluid communication with the tube interior and visible from one of the first tube end or the second tube end, said choke indicating orientation of the at least one aperture.

4. The tube of claim 3 wherein said choke is integral with a starter cap.

5. The tube of claim 1 further comprising a coupler joined to the second tube end by an elongated axial slot in either of the coupler or the second tube and a radially extending pin in the other of the two adapted to fit within the slot and lock the two against circumferential motion relative to one another, and a second tubular section simultaneously engaging said coupler to define a fluid communication channel through said second tubular section, said coupler and said tubular section.

6. The tube of claim 5 further comprising an end cap engaging a second distal end of said second tubular section and precluding air flow through the second distal tube end.

7. An air sampling tube comprising:
   a tubular section having a sidewall defining a tube interior and a tube exterior and at least one aperture providing air communication between the tube interior and the tube exterior, said tube section having a proximal end and a distal end;
   a starter cap having a choke, the choke having a shaped aperture that partially occludes air flow within said starter cap and indicating orientation of the at least one aperture, said starter cap joining said tubular section to a housing containing an air sampling sensor; and
   a coupler or end cap attaching to the distal end of said tubular section.

8. The tube of claim 7 wherein the at least one aperture is an axially extending groove defined by a first edge and a second edge of said sidewall with at least one of the first edge or the second edge enveloped within the tube interior to form an eddy channel adjacent to the groove.

9. The tube of claim 7 comprising a coupler joined to the second tube end in only a single orientation, and a second tubular section simultaneously engaging said coupler to define a fluid communication channel through said second tubular section, said coupler and said tubular section.

10. An air sampling tube comprising:
    a first tubular section having a first sidewall defining a tube interior and a tube exterior and at least one aperture providing air communication between the tube interior and the tube exterior;
    a second tubular section having a second sidewall defining a tube interior and a tube exterior and at least one aperture providing air communication between the tube interior and the tube exterior;
    at least one rotationally asymmetric non-threaded coupler intermediate between said first tubular section and said second tubular section and having a first joinder portion of a semi-cylindrical blade, the blade being friction fit complementary to a first tube end of said first tubular section in a unique rotational position, said coupler having a second joinder portion joined to a second tube end of said second tubular section to form an air communication conduit therethrough with only a single unique rotational orientation between said first tubular section and said second tubular section.

11. The tube of claim 10 wherein said first tubular section is joined in air communication with a housing containing an air sampling sensor.

12. The tube of claim 10 wherein said coupler is formed of thermoplastic, steel, fiberglass, or thermoset resin.

13. The tube of claim 10 wherein said coupler has a non-linear angle between the first joinder portion and the second joinder portion.

* * * * *